Figure 1:
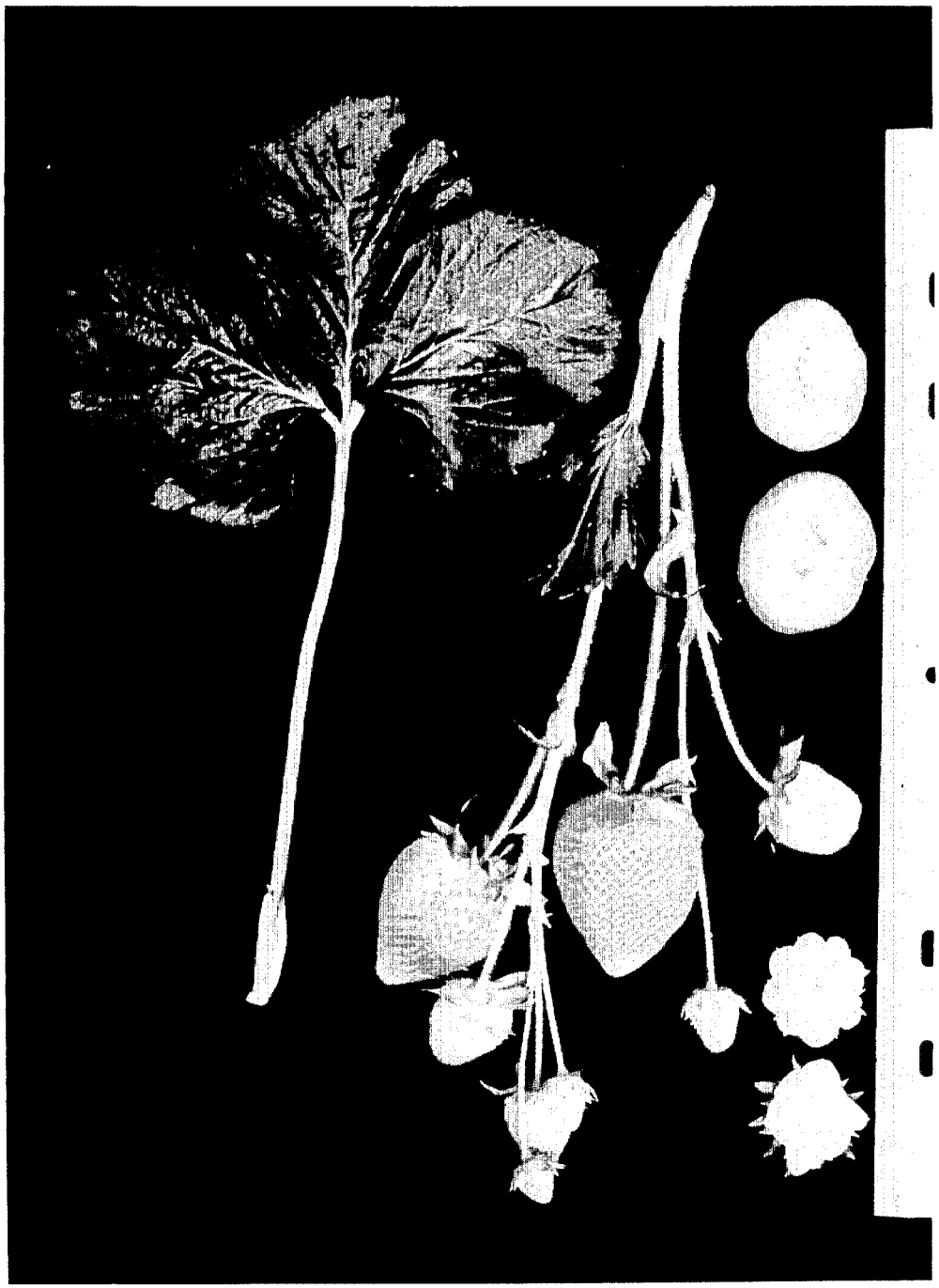

United States Patent [19]

Johnson, Jr.

[11] Plant 4,988

[45] Mar. 8, 1983

[54] STRAWBERRY PLANT

[75] Inventor: Harold A. Johnson, Jr., Watsonville, Calif.

[73] Assignee: Driscoll Strawberry Associates, Inc., Watsonville, Calif.

[21] Appl. No.: 284,919

[22] Filed: Jul. 20, 1981

[51] Int. Cl.[3] ..... A01H 5/03

[52] U.S. Cl. ..... Plt./49

[58] Field of Search ..... Plt./49

*Primary Examiner*—Robert E. Bagwill

*Attorney, Agent, or Firm*—Townsend and Townsend

[57] ABSTRACT

A new and distinct everbearing variety of strawberry plant characterized by fruit which is conic to long wedged. The plant is lacking in berries of irregular shape or which have longitudinal furrows. The plant is further characterized by attachment of fruit to a reflexed calyx and by pedicel hairs which are perpendicular to the pedicel. When planted in January and February, peak production occurs in late July and continues through fall. The berries have a good appearance due to their regular shape, high gloss and consistent color. Fruit flavor equals Heidi in excellence and the berry has a mild pleasant strawberry aroma.

1 Drawing Figure

This invention relates to a new and distinct variety of strawberry plant which is the result of a cross of the Driscoll everbearer selection Z14.106 and Driscoll variety Heidi, U.S. Plant Pat. No. 3,123.

The seedlings resulting from the aforementioned cross were grown and asexually multiplied in Shasta County, Calif. and tested in the fruiting beds on the property of growers of the Driscoll Strawberry Associates, Inc. Clones of the seedlings were also held at the Propagation Nursery in Shasta County. One plant was selected from the aforementioned group of seedlings and further asexually reproduced by runners in the Shasta County nursery of Driscoll Strawberry Associates, Inc. Tests followed in various parts of California during intervening seasons on various properties of grower members of the Driscoll Strawberry Associates, Inc. These tests indicated the merits of the novel plant and resulted in its selection as a promising test variety.

In the drawings:

FIG. 1 illustrates plant parts of the new everbearing variety which are typical in size, shape and color.

Referring to FIG. 1, the berry is shown in cross sections illustrating the flesh color and characteristic core cavity. The inflorescence shown in the drawing is illustrative of typical branching and relative size during the middle of July. The pedicel holding the ripe primary berry originates from the side of one of the two peduncles, but there is often an equal number of pedicels originating from the axil formed at the union of peduncles. There is also a near ripe secondary berry present with its calyx free of the fruit becoming slightly reflexed. The leaf present is typical but there is often a bract present on the petiole. The photographs also show the hair on the pedicels which is growing perpendicular to the pedicel.

The plant of this novel variety is medium in size but vigorous for an everbearer if given ample chilling before being planted. If dug during December at lower elevations in central California it produces at its best when planted the last of January, but commercial production can be realized if planted in late February or March. If planted late January or February its peak production occurs during late July, but will continue in production through the fall.

Some of its distinguishing characteristics are its conic to long wedged fruit attached to a reflexed calyx. The plant is semi-open with dark leaves, darker than the Heidi variety, U.S. Plant Pat. No. 3,123, but not as dark as the Driscoll everbearer E23. The plant is more prostrate than Heidi and the leaves are smaller. The margins of the leaflets are not as deeply serrated as the Heidi or E23. The inflorescence of the new variety are not as abundant as the E23 and the total length is not as great. Flowers above the plant are not as noticeable as that of E23. This ability to produce fewer inflorescence per plant is an asset for an everbearer as the plant is able to maintain a larger minimum fruit size during the late summer when many everbearers produce many small berries. The fruit size of the main crop that starts in late May or June, however isn't as large as E23 or the spring producing variety Heidi. This new variety is also distinct from Heidi and E23 in that its calyx is reflexed, and smaller than Heidi, but equal to E23 in diameter. The seed is usually smaller and darker and is more prone to be inserted within the fruit surface than Heidi or E23. It is less prone to show albino fruit than is E23 or Heidi, (when areas of the fruit surface between seed do not color normally and often become puffy and weak, the condition is referred to as albinism). The pedicels of the new variety are also different in that the hair present is held perpendicular to the pedicel instead of irregularly parallel to the pedicel as is the case with Heidi and E23. Also, the pedicel holding the primary berry is more prone to originate from one of the peduncles than Heidi or E23.

The berry appearance is good, reflecting good pollen production and seed fertilization and the lack of irregular shapes and longitudinal furrows, but at times there are small green tips at the apex of the fruit that are not large enough to distract from fruit appearance. The high gloss and consistent color adds to the appearance of the fruit of the new variety. Even though an everbearer, the new variety is a good runner producer at the nursery.

The flavor is considered excellent, equal to Heidi, but its average rating in panel tests through the year isn't as high as E23. The new variety has a mild, pleasant strawberry odor but not as distinct as E23.

This new variety is not any more susceptible to mildew, Mycosphaerella leaf spot or the two spotted mite than the Heidi variety. It hasn't been tested against the Verticillium wilt or the Red Stele pathogen. As a seedling and selection it withstood the natural invasions of certain virus components found in central California without losing its ability to produce.

The new varietal characteristics of the novel plant, described below in detail, were observed during the first fruiting season. Observations were made during July and August in the Watsonville area of California which is a cool coastal area near the Pacific Ocean. The color terminology is in accordance with the Munsell Color System.

*Plants*: Medium in size and vigorous if given ample chilling before being planted, and has an extensive root system.

*Leaves*: Medium in size. The mature central leaflet is usually 5 to 8 cm. in width and length with the length usually greater than the width. Petioles vary from 15 to 25 cm. in length when measured from their base to the petiolule. Petiolules of central leaflet are medium to long in length averaging 9 mm. Petioles are mostly without bracts, but they may be present on some petioles. Leaflet serrations are not considered deep. The color of the upper side of the leaflet is 0.7 G 3.4/8.5. Phosphogluciosomerase (PGI): similar to Heidi and E23 with the 5 banded pattern called by the University of California the Aiko or A4 pattern 30/35/40 mm. (Scandolios, 1969 Biochem. Genet. 3:37–39).

*Runner*: If plants are dug from low elevation during early December and given mean temperatures near 50° F. during the month of January after a January 1 planting, less than a runner per plant can be expected. The variety is considered a moderate runner producer at the nursery.

*Inflorescence*: Short to medium in length mostly 20 to 25 cm. The hair on a pedicel holding the tertiary flower is perpendicular to the pedicel. A near equal amount of pedicels holding the primary berry originates from the axil formed by the union of peduncles or from one of the peduncles. It is not uncommon to find a portion of the pedicel holding the primary berry fused to the peduncle. Flowers can be observed above the plant and are moderately abundant. Anthers produce an abundance of pollen.

*Fruit*: Primary fruit of the main crop in July are mostly 35 to 45 mm. in length, and 35 to 40 mm. in width. Secondary and tertiary fruit are smaller than primaries, but maintain a high percentage of marketable size even late in the season for an everbearer. The shoulders are rounded, but on some berries when the calyx is reflexed the area near the calyx is almost necked in appearance. The berry in outline is mostly long conic to long wedge as described in the USDA Bulletin 1043. The fruit surface is generally smooth with a minimum amount of roughness or longitudinal furrows, but a small portion of conic tips may not be full colored or becoming white even though the seed at the tips are fertilized. The seeds are small to medium in size and darken in direct sunlight and may be held slightly exerted to sunken. Fruit surface is considered firm, but during periods when seeds are sunken the surface is prone to injury. The fruit has a high dessert quality. The surface color is 6.7 R 3.5/13.1 and the flesh near the epidermis is 6.8 R 4.6/16.5.

*Calyx*: Primaries usually medium in diameter 40 mm. or less and moderately serrated with some overlap. The calyx is often reflexed. Color of the sepals facing the fruit is 7.2 GY 5.1/10.2.

I claim:

1. The new and distinct strawberry plant herein described and illustrated, and identified by the characteristics enumerated above.

* * * * *